United States Patent [19]
Gottfried et al.

[11] 3,944,660
[45] Mar. 16, 1976

[54] PHARMACEUTICAL COMPOSITION
[75] Inventors: Siegfried Gottfried, Ilford; Lily Baxendale, London, both of England
[73] Assignee: Biorex Laboratories, Limited, London, England
[22] Filed: Nov. 28, 1973
[21] Appl. No.: 419,487

[30] Foreign Application Priority Data
Dec. 18, 1972 United Kingdom............. 58354/72

[52] U.S. Cl. .................. 424/44; 424/43; 424/154; 424/155; 424/156; 424/157; 424/158; 424/161; 424/308
[51] Int. Cl.² A61K 9/46; A61K 47/00; A61K 33/06; A61K 31/19
[58] Field of Search............... 424/43, 44, 154–158, 424/308, 161

[56] References Cited
UNITED STATES PATENTS

| | | | |
|---|---|---|---|
| 3,444,290 | 5/1969 | Wai......................... | 424/4 |
| 3,764,618 | 10/1973 | Bonati..................... | 260/448 R |

FOREIGN PATENTS OR APPLICATIONS

| | | |
|---|---|---|
| 628,444 | 8/1963 | Belgium |
| 296,176 | 4/1964 | Spain |

OTHER PUBLICATIONS

Chem. Abst. 60 P 14550f (1964).
Chem. Abst. 63 D 8135g (1965).
Chem. Abst. 71:122296n (1969)(abst. of Laurence et al. Symp. Carbenoxolone Sodium 1967 (pub. 1968) pp. 217–223 "Three–month Assessment of Duogastrone Therapy in Chronic Duodenal Ulcer."]

*Primary Examiner*—Shep K. Rose
*Attorney, Agent, or Firm*—Wenderoth, Lind & Ponack

[57] ABSTRACT

There is provided a pharmaceutical composition in dosage unit form comprising (a) 1 – 100 mg. of glycyrrhetinic acid and/or of at least one anti-inflammatory active derivative thereof, in admixture with (b) 1 – 50% by weight of alginic acid and/or at least one non-toxic salt thereof and/or of at least one carboxyalkyl-cellulose and/or of at least one non-toxic salt thereof, (c) 1 – 30% by weight of at least one non-toxic carbonate and/or bicarbonate and (d) 0 – 30% by weight of at least one antacid compound.

11 Claims, No Drawings

PHARMACEUTICAL COMPOSITION

This application generally relates to subject matter which is similar to that disclosed in applicants' copending application Ser. No. 419,486, filed Nov. 28, 1973.

BACKGROUND OF THE INVENTION

As is well known, glycyrrhetinic acid and several derivatives thereof have valuable anti-inflammatory properties and can be administered topically and orally for the treatment of inflammatory conditions.

In particular, the disodium salt of glycyrrhetinic acid hemisuccinate is extensively used for the treatment of ulcerative conditions of the stomach and duodenum. This disodium salt is described and claimed in U.S. Pat. No. 3,070,623 and a special form of dosage unit containing this disodium salt is described and claimed in U.S. Pat. No. 3,444,290.

Oesophagitis is a common inflammatory condition of the human oesophagus. There are various causes of this inflammatory condition but, broadly speaking, it involves inflammation of the mucous membranes lining the oesophagus.

Although glycyrrhetinic acid and several derivatives thereof are, as mentioned above, widely used in the treatment of inflammatory conditions, they have hitherto not been extensively used for the treatment of human oesophagitis because of the difficulty of ensuring a sufficiently high concentration of the active material in the oesophageal region for a sufficient period of time.

It is, therefore, an object of the present invention to provide a pharmaceutical composition in dosage unit form containing glyrrhetinic acid and/or an anti-inflammatory active derivative thereof which can be used for the treatment of oesophagitis.

SUMMARY OF THE INVENTION

Thus, according to the present invention, there is provided a pharmaceutical composition in dosage unit form which comprises (a) 1 - 100 mg. and preferably 10 - 50 mg. of glycyrrhetinic acid and/or at least one anti-inflammatory active derivative thereof, in admixture with (b) at least one non-toxic carbonate and/or bicarbonate and with (c) alginic acid and/or at least one non-toxic salt thereof and/or with at least one carboxyalkyl-cellulose and/or at least one non-toxic salt thereof.

DETAILED DESCRIPTION OF THE INVENTION

When the alginic acid and/or carboxyalkyl-cellulose component is dispersed in water, a colloidal solution is formed which is very stable. The presence of a carbonate or bicarbonate results in the evolution of carbon dioxide when contacted by an acidic medium, such as is found in the stomach and lower part of the oesophagus. The result is, therefore, that the colloidal solution foams up and floats on top of the contents of the stomach. As a result of the normal reflux from the stomach into the oesophagus, the lower part of the oesophagus fills with a foam which remains in situ for a long period of time, this having been observed in clinical trials by endoscopy. This long-lasting foam in turn ensures that the glycyrrhetinic acid and/or active derivative thereof remains in contact with the inflammatory site for a long period of time and is thus able to exert a prolonged and beneficial effect. Furthermore, the foam results in an excellent distribution of the glycyrrhetinic acid and/or derivative thereof, either in the form of a solution or of a very finely divided dispersion, which, in turn, promotes absorption and adsorption thereof at the inflammatory site.

When the alginic acid is used in the pharmaceutical composition according to the present invention in the form of a salt, the preferred salt is the sodium or potassium salt.

The preferred carboxyalkyl celluloses used according to the present invention contain up to three carbon atoms in the alkyl radical, for example carboxymethyl cellulose, and the non-toxic salts thereof, for example, sodium carboxymethyl cellulose.

Any non-toxic and compatible carbonate or bicarbonate can be used, the preferred compounds being sodium carbonate, sodium bicarbonate, potassium carbonate, potassium bicarbonate, calcium carbonate and magnesium carbonate.

Apart from glycyrrhetinic acid per se, the pharmaceutical composition according to the present invention can also contain known derivatives of glycyrrhetinic acid which inhibit damage to the mucosa of the alimentary tract. Examples of such derivatives of glycyrrhetinic acid include the esters, hemiesters and hemiester salts thereof, especially the disodium salt of glycyrrhetinic acid hemisuccinate (also known as carbenoxolone sodium) (see U.S. Pat. No. 3,070,623 and British Patent Specification Nos. 1,022,968 and 1,032,710); the salts of glycyrrhetinic acid with non-toxic organic bases (see our British Patent Specification Nos. 843,135 and 870,651); the salts of glycyrrhetinic acid and glycyrrhetinic acid hemiesters with bismuth, zinc or a metal of Group IIA, IIIA or VIII of the periodic Table (see our British Patent Specification No. 950,777); the amides of glycyrrhetinic acid and of acylated glycyrrhetinic acid (see U.S. Pat. No. 1,060,344), and the non-toxic metal salts of 3-acetylglycyrrhetinic acid, for example aluminium 3-acetyl-18$\beta$-glycyrrhetinate.

The pharmaceutical composition according to the present invention is in the form of a dosage unit, preferably a tablet, which can have a weight of, for example, from 0.20 - 5.0 g. and preferably of from 0.7 to 2.6 g. Each such dosage unit contains 1 - 100 mg. and preferably 10 - 50 mg. of glycyrrhetinic acid and/or at least one active derivative thereof, 1 - 50% by weight and preferably 10 - 40% by weight of alginic acid and/or of at least one non-toxic salt thereof and/or of at least one carboxyalkyl-cellulose and/or of at least one non-toxic salt thereof and 1 - 30% by weight and preferably 3 - 10% by weight of at least one non-toxic carbonate and/or bicarbonate.

If desired, the pharmaceutical composition according to the present invention can also contain up to 30% by weight and preferably 5 - 15% by weight of at least one antacid compound, i.e., a non-toxic compound which counteracts acidity either by neutralising or buffering acidity, for example, aluminium hydroxide, aluminium phosphate, dihydroxyaluminium aminoacetate, magnesium hydroxide, magnesium trisilicate or the like.

Furthermore, the pharmaceutical composition according to the present invention can contain conventional solid pharmaceutical diluents or carriers, for example, starch, lactose, mannitol, methyl cellulose, talc, highly dispersed silicic acid, gelatine, agar-agar, calcium phosphate, magnesium stearate, animal and vegetable fats and solid high molecular weight polymers (such as polyethylene glycols). If desired, the composition can also comprise at least one flavouring and/or sweetening agent and can also contain or be coated with a colouring material.

The following Examples are given for the purpose of illustrating the present invention:

EXAMPLE 1

Tablet formulation

| | |
|---|---|
| carbenoxolone sodium | 20 mg. |
| mannitol | 400 mg. |
| alginic acid | 200 mg. |
| sodium alginate | 200 mg. |
| aluminium hydroxide, dried gel | 80 mg. |
| sodium bicarbonate | 70 mg. |
| magnesium trisilicate | 20 mg. |
| magnesium stearate | 12 mg. |
| gum acacia | 35 mg. |
| peppermint oil | 2 mg. |
| | 1039 mg. |

EXAMPLE 2

Tablet formulation

| | |
|---|---|
| 18β-glycyrrhetinic acid | 10 mg. |
| mannitol | 150 mg. |
| sucrose | 150 mg. |
| alginic acid | 150 mg. |
| sodium alginate | 150 mg. |
| aluminium hydroxide, dried gel | 80 mg. |
| sodium bicarbonate | 70 mg. |
| magnesium trisilicate | 20 mg. |
| magnesium stearate | 10 mg. |
| gum acacia | 30 mg. |
| peppermint oil | 2 mg. |
| | 822 mg. |

EXAMPLE 3

Tablet formulation

| | |
|---|---|
| carbenoxolone sodium | 20 mg. |
| mannitol | 400 mg. |
| carboxymethyl-cellulose | 200 mg. |
| aluminium hydroxide, dried gel | 80 mg. |
| sodium bicarbonate | 70 mg. |
| magnesium trisilicate | 20 mg. |
| magnesium stearate | 12 mg. |
| gum acacia | 35 mg. |
| peppermint oil | 1 mg. |
| | 838 mg. |

The formulations described above in Examples 1, 2 and 3 are for administration to humans for the treatment and alleviation of oesophagitis.

We claim:

1. A pharmaceutical composition in uncoated tablet dosage unit form useful for treating oesophagitis comprising (a) 1–100 mg. of at least one member selected from the group consisting of glycyrrhetinic acid, the hemiesters thereof, and the salts of the hemiesters, in admixture with (b) 1–50% by weight of at least one member selected from the group consisting of alginic acid, the non-toxic salts of alginic acid, the carboxyalkyl-cellulose and the non-toxic salts of the carboxyalkyl-celluloses, (c) 1–30% by weight of at least one member selected from the group consisting of the non-toxic carbonates and bicarbonates and (d) 0–30% by weight of at least one antacid compound selected from the group consisting of aluminum hydroxide, aluminum phosphate, dihydroxyaluminum aminoacetate, magnesium hydroxide, and magnesium trisilicate, said tablet composition capable of forming a colloidal solution in the stomach, whereby the carbonate or bicarbonate component (c) reacts with the acid medium in the stomach to evolve carbon dioxide gas which foams up the colloidal solution, thereby filling the lower oesophagus with a long lasting foam containing the active glycyrrhetinic acid component (a) which remains in contact with the inflammatory site in the oesophagus for a time sufficient to promote prolonged and beneficial results.

2. A pharmaceutical composition according to claim 1, wherein said uncoated tablet dosage unit has a weight of 0.20 – 5.0 g.

3. A pharmaceutical composition according to claim 1, wherein said uncoated tablet dosage unit has a weight of 0.7 – 2.6 g.

4. A pharmaceutical composition according to claim 1, wherein the glycyrrhetinic acid component (a) is present in an amount of from 10 – 50 mg.

5. A pharmaceutical composition according to claim 1, wherein component (b) is present in an amount of from 10 – 40% by weight.

6. A pharmaceutical composition according to claim 1, wherein component (c) is present in an amount of from 3 – 10% by weight.

7. A pharmaceutical composition according to claim 1, wherein component (d) is present in an amount of from 5 – 15% by weight.

8. A pharmaceutical composition according to claim 1, wherein the glycyrrhetinic acid component (a) is the disodium salt of glycyrrhetinic acid hemisuccinate.

9. A pharmaceutical composition according to claim 1, which additionally comprises at least one member selected from the group consisting of pharmaceutical diluents and carriers, flavouring agents, sweetening agents and colouring materials.

10. A pharmaceutical composition in uncoated tablet dosage unit form, useful for treating oesophagitis comprising (a) 10–50 mg. of the disodium salt of glycyrrhetinic acid hemisuccinate in admixture with (b) 10–40% by weight of alginic acid of carboxymethycellulose (c) 3–10% by weight sodium bicarbonate and (d) 5–15% by weight of at least one antacid compound selected from the group consisting of aluminum hydroxide, aluminum phosphate, dihydroxyaluminum aminoacetate, magnesium hydroxide, and magnesium trisilicate, said tablet composition capable of forming a colloidal solution in the stomach, whereby the carbonate or bicarbonate component (c) reacts with the acid medium in the stomach to evolve carbon dioxide gas which foams up the colloidal solution, thereby filling the lower oesophagus with a long lasting foam containing the active glycyrrhetinic acid component (a) therein, thus ensuring that the active component (a) remains in contact with the inflammatory site in the oesophagus for a time sufficient to promote prolonged and beneficial results.

11. A method of treating oesophagitis, which comprises administering to a human suffering from oesophagitis, a pharmaceutical composition according to claim 1; which composition forms a colloidal solution in the stomach, whereby the carbonate or bicarbonate component (c) reacts with the acid medium in the stomach to evolve carbon dioxide gas which foams up the colloidal solution, thereby filling the lower oesophagus with a long lasting foam containing the active glycyrrhetinic acid component (a) therein, thus ensuring that the active component (a) remains in contact with the inflammatory site in the oesophagus for a time sufficient to promote prolonged and beneficial results.

* * * * *